United States Patent [19]

Sprengeler et al.

[11] Patent Number: 5,519,060

[45] Date of Patent: May 21, 1996

[54] SULFONAMIDE-BASED COMPOSITIONS AND METHODS

[75] Inventors: Paul Sprengeler, Philadelphia; Amos B. Smith, III, Merion; Ralph F. Hirschmann, Blue Bell; Akihisa Yokoyama, Philadelphia, all of Pa.

[73] Assignee: The Trustees of the University of Pennsylvania, Philadelphia, Pa.

[21] Appl. No.: 373,564

[22] Filed: Jan. 17, 1995

[51] Int. Cl.$^6$ .......................... A01N 41/06; A01N 43/00; A61K 31/18; A61K 31/33

[52] U.S. Cl. .......................... 514/601; 514/183; 514/212; 514/218; 514/256; 514/315; 514/357; 514/385; 514/602; 514/605; 435/183; 435/184

[58] Field of Search ........................ 514/183, 212, 514/218, 256, 315, 357, 385, 601, 602, 605; 435/183, 184

[56] References Cited

U.S. PATENT DOCUMENTS

| | | | |
|---|---|---|---|
| 5,444,060 | 8/1995 | Urushibata et al. | 514/256 |
| 5,455,258 | 10/1995 | MacPherson et al. | 514/602 |

OTHER PUBLICATIONS

Askin, D. et al., "Highly Diastereoselective Reaction of Chiral, Non–Racemic Amide Enolate with (s)–Glycidyl Tosylate. Synthesis of the Orally Active HIV-1 Protease Inhibitor L-735,524", *Tetrahedron Letters* 1994, 35, 673-676.

Cheng, Y.-S. et al., "Stability and Activity of Human Immunodeficiency Virus Protease: Comparison of the Natural Dimer with a Homologous, Single–Chain Tethered Dimer", *PNAS USA* 1990, 87, 9660-9664.

Dorsey, B. et al., "L-735,524: The Design of a Potent and Orally Bioavailable HIV Protease Inhibitor", *J. of Med. Chem.* 1994, 37 (21), 3443-3451.

Gallo, R. et al., "Frequent Detection and Isolation of Cytophatic Retroviruses (HTLV-III) from Patients with AIDS and at Risk for AIDS", *Science* 1984, 224, 500-503.

Heimbach, J. et al., "Affinity Purification of the HIV-1 Protease", *Biochem. and Biophys. Res. Comm.* 1989, 164(3), 955-960.

Krohn, A. et al., "Novel Binding Mode of Highly Potent HIV–Proteinase Inhibitors Incorporating the (R)–Hydroxyethylamine Isostere", *J. Med. Chem.* 1991, 34, 3340-3342.

The Merck Index, Eleventh Edition, Budavari, et al. Eds., pp. 1403-1414, Merck & Co., Inc., New Jersey, 1989.

Miyoshi, I. et al., "Type C Virus Particles in a Cord T–Cell Line Derived by Co–Cultivating Normal Human Cord Leukocytes and Human Leukaemic T Cells", *Nature* 1981, 294, 770-771.

Popovic, M. et al., "Detection, Isolation, and Continuous Production of Cytopathic Retroviruses (HTLV-III) from Patients with AIDS and Pre–Aids", *Science* 1984, 224, 497-500.

Roberts, N. et al., "Rational Design of Peptide–Based HIV Proteinase Inhibitors", *Science* 1990, 248, 358-361.

Sarngadharan, M. G. et al., "Antibodies Reactive with Human T-Lymphotropic Retroviruses (HTLV-III) in the Serum of Patients with AIDS", *Science* 1984, 224, 506-508.

Schupach, J. et al., "Serlogical Analysis of a Subgroup of Human T-Lymphotropic Retroviruses (HTLV-III) Associated with AIDS", *Science* 1984, 224, 503-505.

Thompson, W. et al., "Synthesis and Antiviral Activity of a Series of HIV-1 Protease Inhibitors with Functionality Tethered to the $P^1$ or $P^1$, Phenyl Substituents: X–ray Crystal Structure Assisted Design", *J. Med. Chem.* 1992, 35, 1685-1701.

Zhang, Z.-Y. et al., "Dissociative Inhibtion of Dimeric Enzymes", *The J. of Biol. Chem.* 1991, 266(24), 15591-15594.

*Primary Examiner*—Nathan M. Nutter
*Attorney, Agent, or Firm*—Woodcock Washburn Kurtz Mackiewicz & Norris

[57] ABSTRACT

Methods are provided for using 2-hydroxy-3-aminopropyl-sulfonamides to mimic peptides and to modulate the chemical and/or biological activity of enzymes, particularly proteolytic enzymes. Also provided are compositions comprising the sulfonamides in admixture with a pharmaceutically acceptable carrier, adjuvant, or vehicle.

17 Claims, 2 Drawing Sheets

SULFONAMIDE-BASED COMPOSITIONS AND METHODS

GOVERNMENT SUPPORT

Certain of the inventors have been supported by National Institute of General Medical Sciences Grant GM-45611.

FIELD OF THE INVENTION

The present invention relates to the use of 2-hydroxy-3-aminopropylsulfonamides and compositions containing 2-hydroxy-3-aminopropylsulfonamides to, for example, modulate the chemical and/or biological activity of enzymes, particularly proteolytic enzymes.

BACKGROUND OF THE INVENTION peptides are implicated in a wide variety of biochemical processes in humans and other mammals. There are, for example, many known peptidal inhibitors of mammalian enzymes. The design of peptide mimics which are resistant to degradation by proteolytic enzymes has become of increasing interest to peptide chemists. A primary goal has been reduce the susceptibility of mimics to cleavage and inactivation by peptidases while maintaining certain desired biological, chemical, and/or physical properties of a targeted peptide. As a result, the design and synthesis of non-peptidal peptidomimetics has emerged as an enterprise spanning organic, bioorganic, and medicinal chemistry. Frequently, the design and/or synthetic considerations which attend development of peptide mimics are not easily resolved.

There remains a need in the art for metabolically stable chemical compounds which effectively mimic the biological, chemical, and/or physical properties of naturally-occurring or synthetic peptides, particularly those peptides having activity as enzyme inhibitors.

OBJECTS OF THE INVENTION

It is one object of the present invention to provide compounds that mimic the biological and/or chemical activity of peptides.

It is another object to provide compounds that are chemically more stable than peptides, particularly under conditions such as found in the human body.

It is yet another object to provide compounds that modulate (i.e., increase or decrease) the chemical and/or biological activity of enzymes.

It is a further object to provide compounds that function as inhibitors of proteolytic enzymes.

It is another object to provide compositions effective to inhibit enzyme activity.

It is yet another object to provide simple yet efficient methods for synthesizing such compounds.

SUMMARY OF THE INVENTION

These and other objects are accomplished by the present invention, which provides 2-hydroxy-3-aminopropylsulfonamides having formulas I and II:

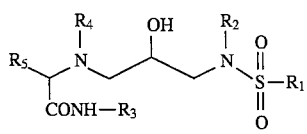

I

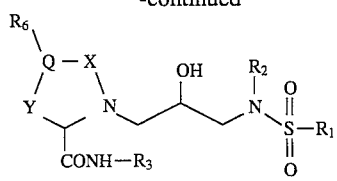

II wherein:

$R_1$ is H, OH, alkyl having 1 to about 10 carbon atoms, or aryl having 3 to about 20 carbon atoms;

$R_2$ is H, alkyl having 1 to about 10 carbon atoms, aryl having 3 to about 20 carbon atoms, alkaryl having 4 to about 25 carbon atoms, or an amino acid side chain;

$R_3$ is H, alkyl having one to about 10 carbon atoms, or alkaryl having 4 to about 25 carbon atoms;

$R_4$ is H, alkyl having 1 to about 10 carbon atoms, aryl having 3 to about 20 carbon atoms, alkaryl having 4 to about 25 carbon atoms, or an amino acid side chain;

$R_5$ is H, alkyl having one to about 10 carbon atoms, or aryl having 3 to about 20 carbon atoms;

$R_6$ is H, alkyl having one to about 10 carbon atoms, aryl having 3 to about 20 carbon atoms, or alkaryl having 4 to about 25 carbon atoms;

X and Y are, independently, alkylene having 1 to about 6 carbon atoms, provided that the sum of X and Y is less than or equal to 9; and Q is N or $CH_2$.

These sulfonamides can be used to modulate the chemical and/or biological activity of enzymes. In particular, the sulfonamides can be used to inhibit proteolytic enzymes, including those associated with human immunodeficiency virus.

The invention also provides methods for modulating the activity of enzymes comprising contacting the enzymes with at least one compound having structure I or II, and compositions comprising the sulfonamides in admixture with a pharmaceutically acceptable carrier, adjuvant, or vehicle. Also provided are methods for treating mammals in need of enzyme modulation comprising administering the sulfonamides of the invention, and methods for mimicking the chemical activity of peptides comprising providing a sulfonamide in place of the peptide.

BRIEF DESCRIPTION OF THE FIGURES

The numerous objects and advantages of the present invention can be better understood by those skilled in the art by reference to the accompanying figures, in which.

DETAILED DESCRIPTION OF THE INVENTION

Figure 1:
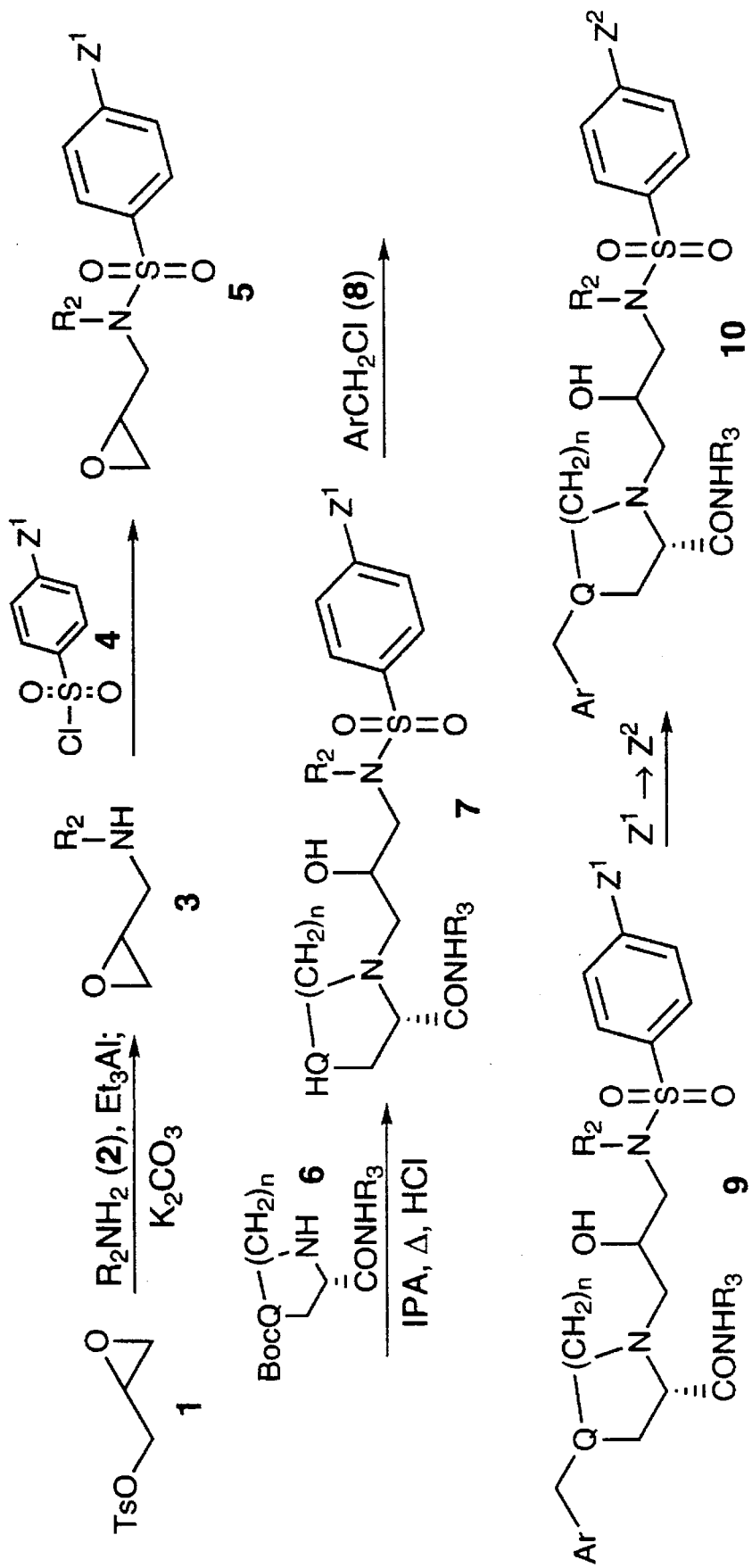
FIG. 1 shows a synthetic scheme for compounds having formula (10).

It has been found in accordance with the present invention that a new class of sulfonamide-based compounds can be used to modulate the chemical and/or biological activity of proteases, including proteases associated with human immunodeficiency virus.

According to certain embodiments of the invention, the sulfonamides of the invention are somewhat linear compounds having formula I:

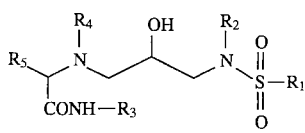

wherein:

R₁ is H, OH, alkyl having 1 to about 10 carbon atoms, or aryl having 3 to about 20 carbon atoms;

R₂ is H, alkyl having 1 to about 10 carbon atoms, aryl having 3 to about 20 carbon atoms, alkaryl having 4 to about 25 carbon atoms, or an amino acid side chain;

R₃ is H, alkyl having one to about 10 carbon atoms, or alkaryl having 4 to about 25 carbon atoms;

R₄ is H, alkyl having 1 to about 10 carbon atoms, aryl having 3 to about 20 carbon atoms, alkaryl having 4 to about 25 carbon atoms, or an amino acid side chain; and R₅ is H, alkyl having one to about 10 carbon atoms, or aryl having 3 to about 20 carbon atoms.

According to other embodiments, the sulfonamides are somewhat cyclic compounds having formula II:

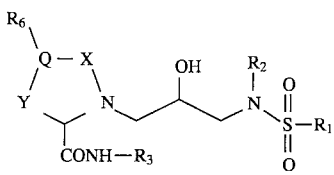

wherein R₁, R₂, R₃, R₄, and R₅ are as defined above and:

R₆ is H, alkyl having one to about 10 carbon atoms, aryl having 3 to about 20 carbon atoms, or alkaryl having 4 to about 25 carbon atoms;

X and Y are, independently, alkylene having 1 to about 6 carbon atoms, provided that the sum of X and Y is less than or equal to 9; and Q is N or CH₂.

Alkyl groups according to the invention include but are not limited to straight chain, branched chain, and cyclic hydrocarbons such as methyl, ethyl, propyl, pentyl, isopropyl, 2-butyl, isobutyl, 2-methylbutyl, and isopentyl moieties having 1 to about 10 carbon atoms, preferably 1 to about 6 carbon atoms. Alkylene groups according to the invention are straight chain or branched chain hydrocarbons that are covalently bound to two other groups. Preferred alkylene groups have the formula —(CH₂)$_n$— where n is 1 to about 6, including methylene (n=1) and ethylene (n=2) groups.

Aryl groups according to the invention are aromatic groups having 3 to about 20 carbon atoms, preferably from 3 to about 10 carbon atoms, including, for example, imidazolyl, naphthyl, phenyl, pyridyl, pyrimidinyl, and xylyl groups and substituted derivatives thereof, particularly those substituted with amino, nitro, hydroxy, methyl, methoxy, thiomethyl, trifluoromethyl, mercaptyl, and carboxy groups. One preferred point for substitution is position Z shown in FIG. 1. Alkaryl groups are groups that contain alkyl and aryl portions and are covalently bound to other groups through the alkyl portion, as in a benzyl group. Aryl groups according to the invention are monocyclic aromatic groups having 3 to about 20 carbon atoms, preferably from 3 to about 10 carbon atoms, including, for example, imidazolyl, naphthyl, phenyl, pyridyl, pyrimidinyl, and xylyl groups and substituted derivatives thereof. Alkaryl groups are groups that contain alkyl and aryl portions and are covalently bound to other groups through the alkyl portion, as in a benzyl group.

The term amino acid as used herein is intended to include all naturally-occurring and synthetic amino acids known in the art. In general, amino acids have structure H₂N—CH(R$_c$)—C(O)OH where R$_c$ is the amino acid side chain. Representative, naturally-occurring side chains are shown in Table 1.

TABLE 1

| | |
|---|---|
| CH₃— | CH₃—CH₂—S—CH₂—CH₂— |
| HO—CH₂— | HO—CH₂—CH₂— |
| C₆H₅—CH₂— | CH₃—CH₂(OH)— |
| HO—C₆H₅—CH₂— | HO₂C—CH₂—NH₂C(O)—CH₂— |
| HO—⟨C₆H₃(OH)⟩—CH₂— | ⟨azetidinyl⟩ |
| ⟨indol-3-yl⟩—CH₂— | HCO₂—CH₂—CH₂— |
| ⟨imidazol-4-yl⟩—CH₂— | NH₂C(O)—CH₂—CH₂— |
| HS—CH₂— | (CH₃)₂—CH— |
| HO₂C—CH(NH₂)—CH₂—S—S—CH₂— | (CH₃)₂—CH—CH₂— |
| CH₃—CH₂— | CH₃—CH₂—CH₂— |
| CH₃—S—CH₂—CH₂— | H₂N—CH₂—CH₂—CH₂— |
| | H₂N—C(NH)—NH—CH₂—CH₂—CH₂— |
| | H₂N—C(O)—NH—CH₂—CH₂—CH₂— |
| | CH₃—CH₂—CH(CH₃)— |
| | CH₃—CH₂—CH₂—CH₂ |

TABLE 1-continued

Preferred side chains include $(CH_3)_2$—CH—, $(CH_3)_2$—CH—$CH_2$—, $C_6H_5$—$CH_2$—, and $R_fC(O)C(O)$—$(CH_2)_z$—O—$C_6H_5$—$CH_2$— where z is 1 to about 10 (preferably 1–6) and $R_f$ is H or alkyl having 1 to about 12 carbon atoms.

The sulfonamides of the invention contain amino groups and, therefore, are capable of forming salts with various inorganic and organic acids. Such salts are also within the scope of this invention. Representative salts include acetate, adipate, benzoate, benzenesulfonate, bisulfate, butyrate, citrate, camphorate, camphorsulfonate, ethanesulfonate, fumarate, hemisulfate, heptanoate, hexanoate, hydrochloride, hydrobromide, hydroiodide, methanesulfonate, lactate, maleate, methanesulfonate, 2-naphthalenesulfonate, nitrate, oxalate, pamoate, persulfate, picrate, pivalate, propionate, succinate, sulfate, tartrate, tosylate, and undecanoate. The salts can be formed by conventional means, such as by reacting the free base form of the product with one or more equivalents of the appropriate acid in a solvent or medium in which the salt is insoluble, or in a solvent such as water which is later removed in vacuo or by freeze drying. The salts also can be formed by exchanging the anions of an existing salt for another anion on a suitable ion exchange resin.

In one aspect, the present invention provides methods for modulating enzyme activity comprising contacting a compound of the invention with an enzyme of interest. Preferred enzymes are proteolytic enzymes including but not limited to those associated with human immunodeficiency virus. As used herein, the term "contacting" means directly or indirectly causing placement together of moieties to be contacted, in vitro or in vivo, such that the moieties come into physical contact with each other. Contacting thus includes physical acts such as placing the moieties (e.g., compound and enzyme-containing cell) together in a container or administering moieties to a patient.

Also provided are prophylactic, diagnostic, and therapeutic compositions comprising one or more of the compounds of the invention. By administering an effective amount of such compositions, for example, prophylactic or therapeutic responses can be produced in a human or some other type of mammal. It will be appreciated that the production of prophylactic or therapeutic responses includes the initiation or enhancement of desirable responses, as well as the cessation or suppression of undesirable responses. It is believed that the compounds of the invention can be used to inhibit the chemical and/or biological activity of a wide variety of enzymes, particularly protease enzymes including those associated with the human immunodeficiency virus.

Compositions for use in the methods of this invention can be in the form of a solid, semisolid or liquid form and can include one or more of sulfonamide compounds as an active ingredient in admixture with an organic or inorganic carrier or excipient suitable for external, enteral or parenteral applications. The active ingredient can be compounded, for example, with the usual non-toxic, pharmaceutically acceptable carriers for tablets, pellets, capsules, suppositories, solutions, emulsions, suspensions, and any other form suitable for use. The carriers which can be used are water, glucose, lactose, gum acacia, gelatin, mannitol, starch paste, magnesium trisilicate, talc, corn starch, keratin, colloidal silica, potato starch, urea and other carriers suitable for use in manufacturing preparations, in solid, semisolid, or liquid form, and in addition auxiliary, stabilizing, thickening and coloring agents and perfumes maybe used. The active ingredient is included in the pharmaceutical composition in an amount sufficient to produce the desired effect upon the process or condition of diseases.

For oral administration, tablets containing various excipients such as microcrystalline cellulose, sodium citrate, calcium carbonate, dicalcium phosphate and glycine may be employed along with various disintegrants such as starch and preferably corn, potato or tapioca starch, alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of sulfonamide-based compounds in either sesame or peanut oil or in aqueous propylene glycol can be employed. The aqueous solutions should be suitably buffered (preferably pH>8) if necessary and the liquid diluent first rendered isotonic. These aqueous solutions are suitable for intravenous injection purposes. The oily solutions are suitable for intra-articular, intra-muscular and subcutaneous injection purposes. The preparation of all these solutions under sterile conditions is readily accomplished by standard pharmaceutical techniques well-known to those skilled in the art. Additionally, it is possible to administer the compounds of the present invention topically when treating inflammatory conditions of the skin and this may preferably be done by way of creams, jellies, gels, pastes, ointments and the like, in accordance with standard pharmaceutical practice.

The amount of active ingredient that may be combined with the carrier materials to produce a single dosage form will vary depending upon the host treated and the particular mode of administration. The specific dose level for any particular patient will depend on a variety of factors including the activity of the specific compound employed, the age, body weight, general health, sex, diet, time of administration, route of administration, rate of excretion, drug combination, and the severity of the particular disease undergoing therapy. In some instances, dosage levels below the lower limit of the aforesaid range may be more than adequate, while in other cases still larger doses may be employed without causing any harmful side effects provided that such higher dose levels are first divided into several small doses for administration throughout the day.

For treatment of patients infected with human immunodeficiency virus, the sulfonamide-based compounds of the invention are administered to a patient in an amount to be determined empirically by one skilled in the art of such therapy, using as a guideline, the concentration of sulfonamide-based compound necessary for inhibition of protease activity and inhibition of virus spread in cell culture assays. These assays are set forth in detail below. Because the extent of treatment of any infected individual will vary depending upon the virus load they carry, their level of immune competence, their age, the number of years they have been infected and other factors, the exact protocol to be used in any one individual will be determined on a case by case basis.

In one aspect, the present invention also provides antibacterial compositions comprising one or more sulfonamide compounds, as well as methods for inactivating (e.g., killing) bacteria by contacting them with a compound according to the invention or a composition comprising a compound according to the invention. The compositions of the invention include one or more of sulfonamide compounds as an active ingredient in admixture with a suitable organic or inorganic carrier or excipient. One anticipated use of the claimed compounds involves inactivating bacteria suspected to be borne on food preparation surfaces or other objects by contacting such objects with a composition of the invention. Solutions containing sulfonamide compounds are prepared for such uses by dissolving the sulfonamide in a suitable (preferably volatile) organic solvent such as methanol, ethanol, propanol, dimethylsulfoxide, ethyl ether, dimethylformamide, tetrahydrofuran, acetonitrile, petroleum ether, hexanes, benzene, methylene chloride, chloroform, carbon tetrachloride, and pyridine. Aqueous solutions are prepared by dissolving the sulfonamide or its salt (and, optionally, a surfactant) in water or some other aqueous medium. Surfactants according to the invention are compounds that modify the surface tension of the aqueous system and facilitate dissolution of the sulfonamide and/or its salt. Sulfonamides also can be compounded, for example, with the usual non-toxic, pharmaceutically acceptable carriers for tablets, pellets, capsules, suppositories, solutions, emulsions, suspensions, and any other form suitable for therapeutic use. The active ingredient is included in the composition in an amount sufficient to produce the desired antibacterial or antimicrobial effect.

Additional objects, advantages, and novel features of this invention will become apparent to those skilled in the art upon examination of the following examples thereof, which are not intended to be limiting.

EXAMPLE 1

General Synthesis Of Compounds Having Formula (10).

A. (S)- or (R)-N-Glycidyl N-alkylamine (3).

As shown in FIG. 1, to a stirred solution of alkylamine (2) (5.0 mmol) and dichloromethane (15 mL) under argon is added triethylaluminum (3.2 mL, 1.55M in toluene) dropwise over about 5 minutes. (R)- or (S)-Glycidyl tosylate (1) (5.0 mmol) is added after 30 minutes and the reaction mixture is allowed to stir overnight at room temperature. After carefully quenching the reaction mixture by dropwise addition of 6M sodium hydroxide (4 mL) the mixture is stirred for about 1–2 hours. The layers are separated and the aqueous phase is extracted with dichloromethane, dried over sodium sulfate, and concentrated in vacuo. The residue is dissolved in dry methanol (100 mL) and anhydrous potassium carbonate (3.1 g, 22 mmol) is added at room temperature. The mixture is stirred for 3 hours, poured into brine (500 mL), and the aqueous layer is extracted with chloroform (3 x). The dried residue is purified via flash chromatography to afford (S)- or (R)-N-glycidyl N-alkylamine (3).

B. (S)- or (R)-N-Glycidyl N-alkyl-4-$X^1$-benzene-sulfonamide (5).

To (S)- or (R)-N-glycidyl N-alkylamine (3) (5 mmol) in pyridine (50 mL) at 55°–65° C. is added slowly 4-$X^1$-benzene-sulfonyl chloride (4) (5.1 mmol). The mixture is allowed to stir for 4–6 hours at 55°–65° C. and the pyridine is then removed in vacuo and the residue purified by flash chromatography to afford (S)- or (R)-N-glycidyl N-alkyl-4-$X^1$-benzenesulfonamide (5).

C. 2(S)- or 2(R)-1-[N-Alkyl-N-(4-$X^1$-benzene-sulfonyl)amino] -3-[1-[2(S)-(N-tert-butylcarbamoyl)aminocyclic]]-2-propanol (7).

(S)- or (R)-N-Glycidyl N-alkyl-4-$X^1$-benzenesulfonamide (5) (5 mmol) and N-tert-butyl-4-[(1,1-dimethylethoxy)-carbonyl]aminocyclic-2(S)-carboxamide (6) (5.4 mmol) are dissolved in isopropanol (100 mL) and allowed to stir at 85° C. for 60 hours. The mixture is concentrated in vacuo and the residue (if necessary) is dissolved in isopropanol (35 mL) and treated with 6N HCl (40 mL) at 0° C. for 1 hour. The mixture is stirred an additional 6 hours at room temperature, cooled to 0° C., carefully quenched with 5N NaOH until pH 10, and partitioned between ethyl acetate and water. The aqueous phase is extracted with ethyl acetate and the combined organic phases washed with water and brine, dried over magnesium sulfate, concentrated in vacuo, and purified by flash chromatography to afford 2(S)- or 2 (R)-1-[N-alkyl-N-(4-$X^1$-benzenesulfonyl)amino]-3-[1-[2(S)-(N-tert-butylcarbamoyl)aminocyclic]]-2-propanol (7).

D. 2(S)- or 2(R)-1-[N-Alkyl-N-(4-$X^1$ -benzene-sulfonyl)amino]-3-[1-4-(arylmethyl)-2 (S)-(N-tert-butylcarbamoyl)aminocyclic]]-2-propanol (9).

To 2 (S)- or 2 (R)-1-[N-alkyl-N-(4-$X^1$-benzenesulfonyl)amino]-3-[1-[2(S)-(N-tert-butylcarbamoyl) aminocyclic]]-2-propanol (7) (5 mmol) in DMF (10.5 mL) is added arylmethyl chloride (8) (5.5 mmol) and triethylamine (1.54 mL, 11 mmol). After 12 hours, the reaction mixture is diluted with ethyl acetate (100 mL) washed with water and brine, dried over magnesium sulfate, concentrated in vacuo, and purified by flash chromatography to afford 2(S)- or 2(R)-1-[N-alkyl-N-(4-$X^1$ -benzenesulfonyl)amino]-3-[1-[4-(arylmethyl)-2 (S)-(N-tertbutylcarbamoyl)aminocyclic]]-2-propanol (9).

E. 2(S)- or 2(R)-1-[N-Alkyl-N-(4-$X^1$ -benzenesulfonyl)amino]-3-[1-[4-(arylmethyl)-2 (S)-(N-tert-butylcarbamoyl)aminocyclic]]-2-propanol (10).

The protecting group on the benzenesulfonyl moiety of 2(S)- or 2(R)-1-[N-Alkyl-N-(4-$X^1$-benzenesulfonyl)amino] -3 -[1-[4-(arylmethyl)-2(S)-(N-tert-butylcarbamoyl)aminocyclic]]-2-propanol (9) is deprotected (if necessary) using standard procedures to afford 2(S)- or 2(R)-1-[N-alkyl-N-(4-$X^3$ -benzenesulfonyl)amino]-3-[1-[4-(arylmethyl)-2 (S)-(N-tert-butylcarbamoyl)aminocyclic]]-2-propanol (10).

EXAMPLE 2

Specific Synthesis Of Diastereomers Having Formula 19.

A. N-iso-Butyl-allylamine (11).

Figure 2:
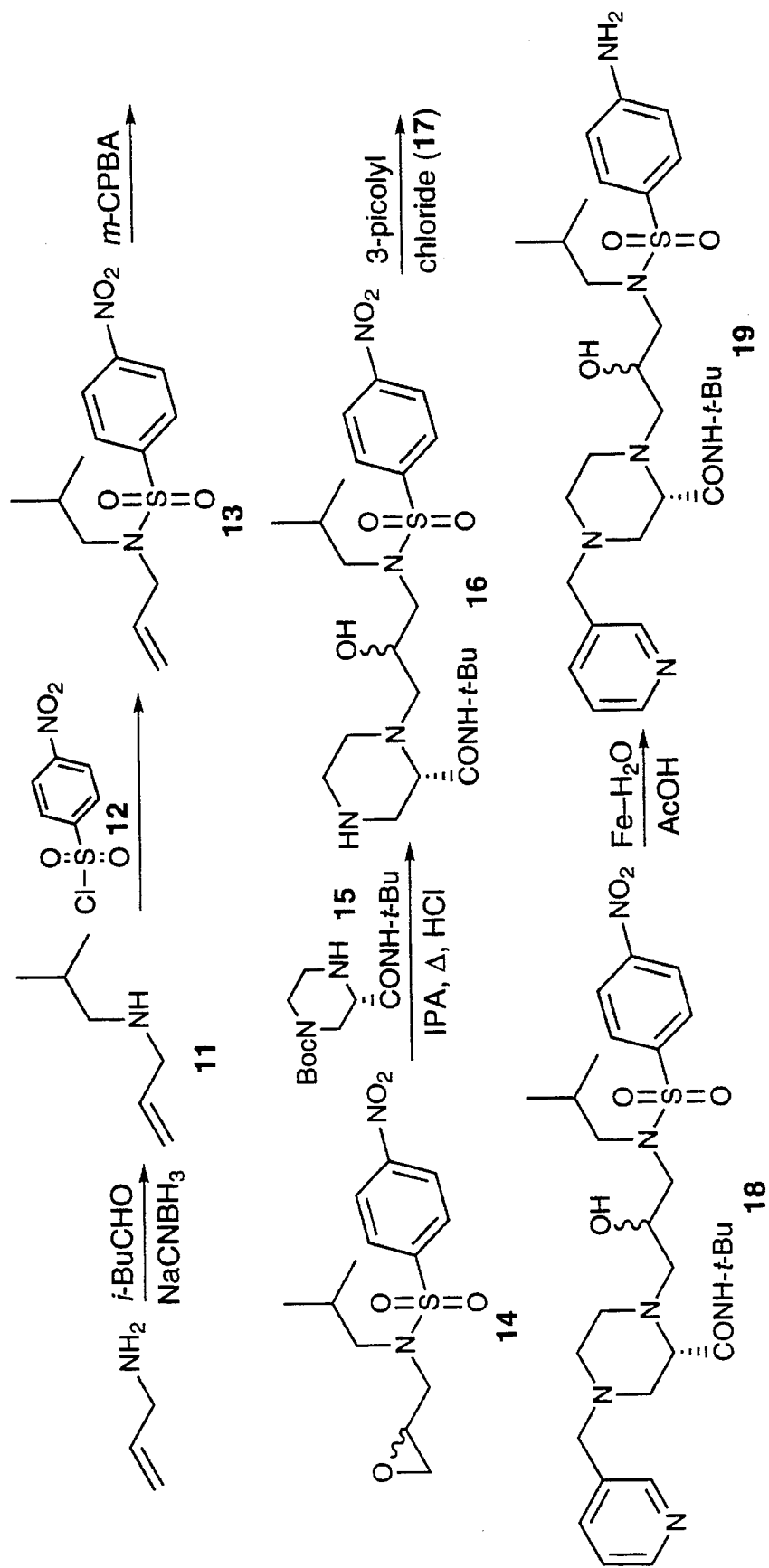
FIG. 2 shows a synthetic scheme for compounds having formula (19).

As shown in FIG. 2, to allylamine (5 mmol) in methyl alcohol (30 mL) at room temperature is added sodium cyanoborohydride (3.6 mg, 5.6 mmol). After stirring for 10 minutes, isobutyraldehyde (5 mmol) is added and the mixture is stirred for an additional 72 hours. Filtration and washing with methyl alcohol and ethyl ether is followed by drying with magnesium sulfate, concentration in vacuo, and purification by flash chromatography to affords N-iso-butyl-allylamine (11).

B. N-Allyl-N-iso-butyl-4-nitrobenzenesulfonamide (13).

To N-iso-Butyl-allylamine (11) (5 mmol) in pyridine (50 mL) at 55°–65° C. is added slowly 4-nitrobenzenesulfonyl chloride (12) (5.1 mmol). The mixture is allowed to stir for 4–6 hours at 55°–65° C. and the pyridine is then removed in vacuo and the residue purified by flash chromatography to afford N-allyl-N-iso-butyl-4-nitrobenzenesulfonamide (13).

C. N-iso-Butyl-N-2(S)- and 2(R)-glycidyl-4-nitrobenzenesulfonamide (14).

To N-allyl-N-iso-butyl-4-nitrobenzenesulfonamide (13) (5 mmol) in dichloromethane (7 mL) is added sodium bicarbonate (2.0 g, 22 mmol). Upon stirring at room temperature for 5 minutes, meta-chloroperbenzoic acid (2.0 g, 22 mmol) is added and heated at reflux for 24 hours. The mixture is poured into saturated aqueous sodium sulfite (7 mL) and the aqueous layer is extracted with ethyl ether. The combined organic layers are dried over magnesium sulfate, concentrated in vacuo, and purified by flash chromatography to afford N-iso-butyl-N-2(S)- and 2(R)-glycidyl-4-nitrobenzenesulfonamide (14).

D. 2(S)- and 2(R)-1-[N-iso-Butyl-N-(4-nitrobenzenesulfonyl)amino] -3-[1-[2(S)-(N-tert-butylcarbamoyl)piperazinyl]]-2-propanol (16).

N-iso-Butyl-N-2(S)- and 2(R)-glycidyl-4-nitrobenzenesulfonamide (14) (5 mmol) and N-tert-butyl-4-[(1,1-dimethylethoxy)carbonyl] piperazine-2(S)-carboxamide (15) (5.4 mmol) are dissolved in isopropanol (100 mL) and allowed to stir at 85° C. for 60 hours. The mixture is concentrated in vacuo and the residue is dissolved in isopropanol (35 mL) and treated with 6N HCl (40 mL) at 0° C. for 1 hour. The mixture is stirred an additional 6 hours at room temperature, cooled to 0° C., carefully quenched with 5N NaOH until pH 10, and partitioned between ethyl acetate and water. The aqueous phase is extracted with ethyl acetate and the combined organic phases washed with water and brine, dried over magnesium sulfate, concentrated in vacuo, and purified by flash chromatography to afford 2(S)- and 2(R)-1-[N-iso-butyl-N-(4 -nitrobenzenesulfonyl)amino] -3-[1-[2(S)-(N-tert-butylcarbamoyl)piperazinyl]]-2-propanol (16).

E. 2(S)- and 2(R)-1-[N-iso-Butyl-N-(4-nitrobenzenesulfonyl)amino] -3-[1-[4-(3-pyridylmethyl)-2(S)-(N-tert-butyl carbamoyl)piperazinyl]]-2-propanol (18).

To 2(S)- and 2(R)-1-[N-iso-butyl-N-(4-nitrobenzenesulfonyl)amino] -3-[1-[2(S)-(N-tert-butylcarbamoyl)piperazinyl] ]-2-propanol (16) (5 mmol) in DMF (10.5 mL) is added 3-picolyl chloride hydrochloride salt (17) (907 mg, 5.5 mmol) and triethylamine (1.54 mL, 11 mmol). After 12 hours, the reaction mixture is diluted with ethyl acetate (100 mL) washed with water and brine, dried over magnesium sulfate, concentrated in vacuo, and purified by flash chromatography to afford 2(S)- and 2(R)-1-[N-iso-butyl-N-(4-nitrobenzenesulfonyl)amino] -3-[1-[4-(3-pyridylmethyl)-2(S)-(N-tert-butyl carbamoyl)piperazinyl]]-2-propanol (18).

F. 2(S)- and 2(R)-1-[N-iso-Butyl-N-(4-sulfanilyl)amino] -3-[1-[4-(3-pyridylmethyl)-2(S)-(N-tert-butylcarbamoyl ) piperazinyl]]-2-propanol (19).

To Fe-H$_2$O suspension containing a trace of acetic acid is added 2(S)- and 2(R)-1-[N-iso-butyl-N-(4-nitrobenzenesulfonyl)amino] -3-[1-[4-(3-pyridylmethyl)-2(S)-(N-tert-butyl carbamoyl)piperazinyl]]-2-propanol (18). The mixture is diluted with an equal volume of ethyl alcohol and excess ammonium hydroxide and subsequently filtered. The filtrate is concentrated in vacuo and acidified with acetic acid to pH 6 followed by purification by flash chromatography to afford 2(S)- and 2(R)-1-[N-iso-butyl-N-(4-sulfanilyl)amino]-3-[1-[4-(3-pyridylmethyl)-2(S)-(N-tert-butylcarbamoyl)piperazinyl]]-2-propanol (19).

EXAMPLE 3

The extent to which the compounds of the invention inhibit HIV protease and prevent the spread of HIV is determined generally according to the methods disclosed by Thompson, et al., *J. Med. Chem.* 1992, 35, 1685. IC$_{50}$ and CIC$_{95}$ values are determined using HIV-1 protease purified generally according to Heimbach, et al., *Biochem. Biophys. Res. Commun.* 1989, 164, 955. Essentially, inhibition of cleavage of a peptide, for example, H-Val-Ser-Gln-Asn-(L-β-napthyalanine)-Pro-Ile-Val-OH, is assessed at about 30° C., pH about 5.5, at an enzyme concentration of about 30 pM for about 1 hour, using HPLC. Products are detected using UV light. To obtain IC$_{50}$ data, a substrate concentration of about 0.4 mg/ml is used. K$_i$ data is determined from double reciprocal plots of rate data as a function of substrate and inhibitor concentrations. The dissociation of subunits from the active, dimeric form of the enzyme to inactive monomers has a K$_d$ of 50 nM at pH 7.0 (Cheng, et al., *Proc. Natl. Acad. Sci. USA* 1990, 87, 9660) and a K$_d$ of 3.6 nM at pH 5.0 (Zhang, et al., *J. Biol. Chem.* 1991, 266, 15591), using kinetic methods. Steady state kinetic treatment of an obligatory active dimer predicts that both the specific activity and K$_i$ should be a function of enzyme concentration and K$_d$.

To assess inhibition of spread of HIV infection following administration of the compounds of the invention, the compound to be tested is dissolved in a solvent such as dimethyl sulfoxide, ethanol, methanol, or propanol, and then serially diluted in cell culture medium. Cells are treated with the test compound either prior to, concurrently with, or post-infection with HIV. Cells are infected with HIV at a multiplicity of infection of about 0.01 infectious units and are subsequently grown in culture medium. Generally, fresh test compound is added at the time of infection and periodically thereafter; for example, every 2 to 3 days postinfection.

Cells which are useful in an HIV assay are H9 (Popovic, et al., Science 1984, 224, 497) and MT-4 human T lymphoid cells (Miyoshi, et al., Nature 1981, 294, 770). In addition, primary peripheral blood lymphocytes and primary monocytes/macrophages may be used. When these latter cells are used, in general, they are obtained from fresh human plasmapheresis residues; they are separated from lymphocytes by adherence to plastic and are maintained in GM-CSF-containing medium. Prior to virus infection, lymphocytes are activated with phytohemaglutinin. Measurement of virus spread is generally accomplished in a fixed cell immunofluorescence assay using anti-HIV human serum or in an ELISA assay using p24. In the immunofluorescence assay, the lowest concentration which prevents spread of virus at 7–24 days post-infection is considered to be the CIC (cell culture minimal inhibitory concentration). In the ELISA assay, the CIC is generally that concentration which inhibits virus spread by greater than 95% (i.e., a greater than 95% reduction in p24 production) relative to untreated controls.

Those skilled in the art will appreciate that numerous changes and modifications may be made to the preferred embodiments of the invention and that such changes and modifications may be made without departing from the spirit of the invention. It is therefore intended that the appended claims cover all such equivalent variations as fall within the true spirit and scope of the invention.

What is claimed is:

1. A method for modulating the activity of an enzyme, comprising contacting said enzyme with at least one compound having structure I or II:

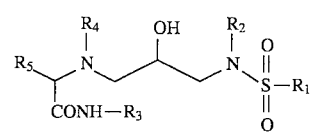

I

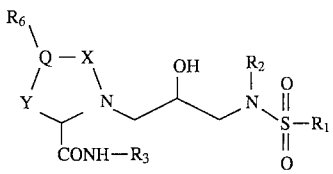

II wherein:

R₁ is H, OH, alkyl having 1 to about 10 carbon atoms, or aryl having 3 to about 20 carbon atoms;

R₂ is H, alkyl having 1 to about 10 carbon atoms, aryl having 3 to about 20 carbon atoms, alkaryl having 4 to about 25 carbon atoms, or an amino acid side chain;

R₃ is H, alkyl having one to about 10 carbon atoms, or alkaryl having 4 to about 25 carbon atoms;

R₄ is H, alkyl having 1 to about 10 carbon atoms, aryl having 3 to about 20 carbon atoms, alkaryl having 4 to about 25 carbon atoms, or an amino acid side chain;

R₅ is H, alkyl having one to about 10 carbon atoms, or aryl having 3 to about 20 carbon atoms;

R₆ is H, alkyl having one to about 10 carbon atoms, aryl having 3 to about 20 carbon atoms, or alkaryl having 4 to about 25 carbon atoms;

X and Y are, independently, alkylene having 1 to about 6 carbon atoms, provided that the sum of X and Y is less than or equal to 9; and Q is N or CH₂.

2. The method of claim 1 wherein said enzyme is a protease.

3. The method of claim 1 wherein said enzyme is a protease associated with human immunodeficiency virus.

4. The method of claim 1 wherein said contacting decreases the activity of said enzyme.

5. The method of claim 1 wherein R₁ is aryl.

6. The method of claim 1 wherein R₂ is aminophenyl.

7. The method of claim 1 wherein R₂ is aryl.

8. The method of claim 1 wherein R₂ is isopropyl.

9. The method of claim 1 wherein R₃ is t-butyl.

10. The method of claim 1 wherein X and Y are, independently, alkylene having 1 to about 3 carbon atoms.

11. The method of claim 1 wherein X is ethylene.

12. The method of claim 1 wherein Y is methylene.

13. The method of claim 1 wherein Q is N.

14. The method of claim 1 wherein R₆ is alkaryl.

15. The method of claim 1 wherein R₆ is picolyl.

16. The method of claim 1 wherein R₁ is aryl, R₂ is alkyl, R₃ is alkyl, X and Y are, independently, alkylene having 1 to about 3 carbon atoms, Q is N, R₆ is alkaryl.

17. The method of claim 1 wherein said compound has structure:

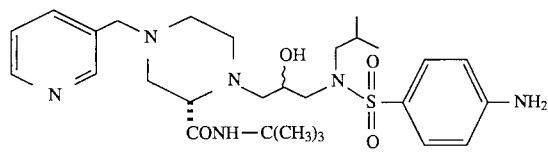

\* \* \* \* \*